United States Patent
Chen

[11] Patent Number: 5,820,619
[45] Date of Patent: Oct. 13, 1998

[54] SANITARY NAPKIN WITH HUMP AND GROOVE

[76] Inventor: Chuan Mei Chen, P.O. Box 82-144, Taipei, Taiwan

[21] Appl. No.: 904,181

[22] Filed: Aug. 1, 1997

[51] Int. Cl.[6] .................................................. A61F 13/15
[52] U.S. Cl. .................................... 604/385.1; 604/358
[58] Field of Search .............................. 604/385.1, 358, 604/374, 378, 386, 387

[56] References Cited

U.S. PATENT DOCUMENTS

| | | | |
|---|---|---|---|
| 2,064,431 | 12/1936 | Jurgenson | 604/385.1 |
| 2,331,355 | 10/1943 | Strongson | 604/385.1 |
| 2,662,527 | 12/1953 | Jacks | 604/374 |
| 2,747,575 | 5/1956 | Mercer | 604/385.1 |
| 4,631,062 | 12/1986 | Lessen et al. | 604/378 |
| 5,342,337 | 8/1994 | Runeman et al. | 604/385.1 |
| 5,665,081 | 9/1997 | Grosse | 604/385.1 |

*Primary Examiner*—Mark O. Polutta
*Attorney, Agent, or Firm*—A & J

[57] ABSTRACT

A sanitary napkin includes a body provided with a plurality of reinforcing elements thereon and having a stop element at one end thereof. The stop element is flat and arched, which may be held in a depressed portion of the coccyx area of the user to absorb any menstrual discharge flowing to the coccyx area. The body is further provided with a groove for receiving the stop element when the sanitary napkin is folded.

1 Claim, 4 Drawing Sheets

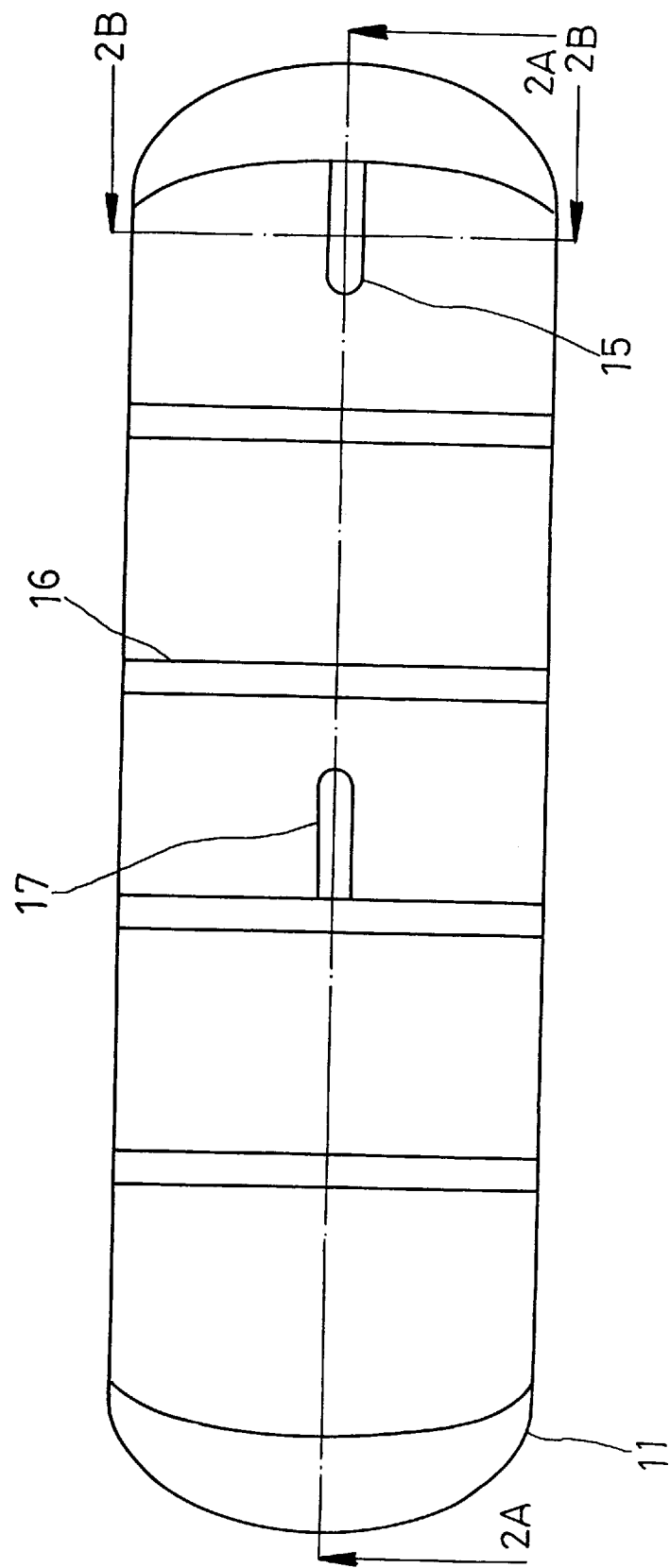

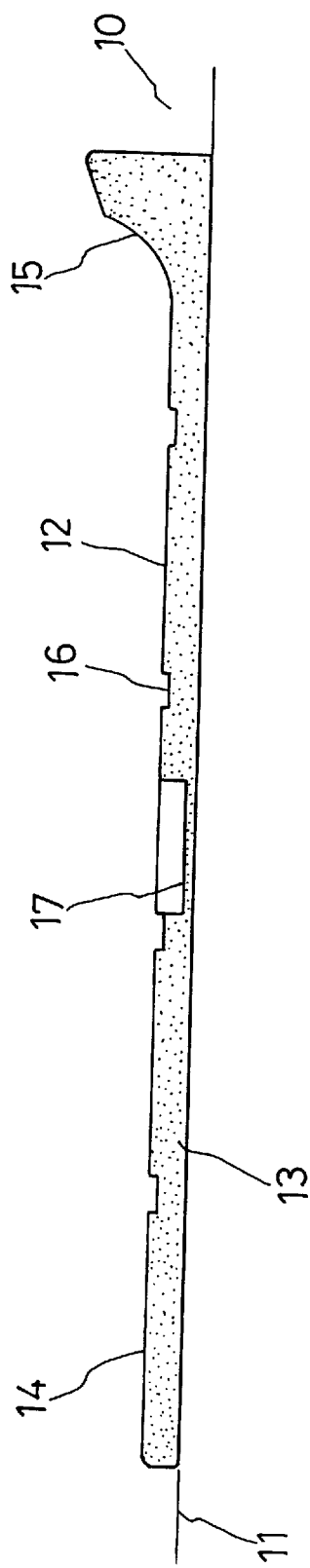
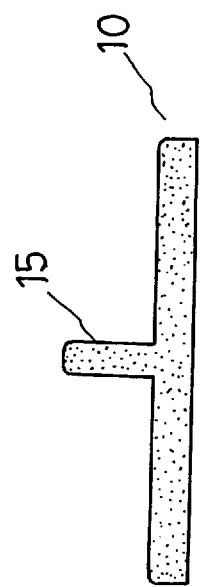
FIG. 2A
FIG. 2B

SANITARY NAPKIN WITH HUMP AND GROOVE

BACKGROUND OF THE INVENTION

1. Field of the Invention

This invention relates generally to an improved sanitary napkin structure, and more particularly to a sanitary napkin which may prevent menstrual discharge from flowing to the coccyx area.

2. Description of the Prior Art

Various types of sanitary napkins are available on the market. Among them, there is a spoon type sanitary napkin which comprises a rectangular front half and an oval rear half. The spoon type sanitary napkin structure is characterized in that the oval rear half is provided with a raised portion at a central portion thereof, the raised portion being thicker than the rectangular front half and becoming thinner towards the periphery of the oval rear half, thus forming a support means which the user may insertably place at an inwardly curved portion at the coccyx area.

In a way, the above-described sanitary napkin structure may effectively prevents menstrual discharge from flowing backwardly to the coccyx area. But since the structure and shape of the oval rear half is not satisfactory, when it is insertably placed at coccyx area, it will project from the user's hips, especially when the user's wear tights or thin clothes, which is very unsightly. Furthermore, the rectangular front half which is placed between the user's legs will very often be bent inwardly as with conventional sanitary napkins.

SUMMARY OF THE INVENTION

This invention relates generally to an improved sanitary napkin structure, and more particularly to a sanitary napkin which may prevent menstrual discharge from flowing to the coccyx area.

Accordingly, a primary object of the present invention is to provide a sanitary napkin structure which may effectively prevent menstrual discharge from flowing to the coccyx area.

Another object of the present invention is to provide a sanitary napkin which will not easily be bent inwardly under prolonged use.

In order to achieve the above-mentioned objects, the sanitary napkin according to the present invention essentially comprises a body having a water absorbent flat stop element at one end thereof, the stop element being held below the coccyx during use. The stop element may absorb any menstrual discharge flowing to the coccyx area. Besides, since the stop element is virtually concealed at a depressed portion of the coccyx area during use, the entire sanitary napkin appears like ordinary sanitary napkin during use, without affecting the natural contour of the buttocks of the user.

Furthermore, the body of the sanitary napkin is provided with a groove for matching the stop element so that the sanitary napkin may remain flat when folded. The stop element is received in the groove when the body of the sanitary napkin is folded so that it will not project upwardly when the body is folded.

In addition, the body of the sanitary napkin is horizontally provided with a plurality of reinforcing elements so that the sanitary napkin will not easily deform in shape or be bent during use.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

BRIEF DESCRIPTION OF THE DRAWINGS

FIG. 1 is a schematic view of the structure of the sanitary napkin of the present invention;

FIG. 2A is a sectional view taken along line A—A of FIG. 1;

FIG. 2B is a sectional view taken along line B—B of FIG. 1;

DETAILED DESCRIPTION OF THE PREFERRED EMBODIMENT

Figure 3:
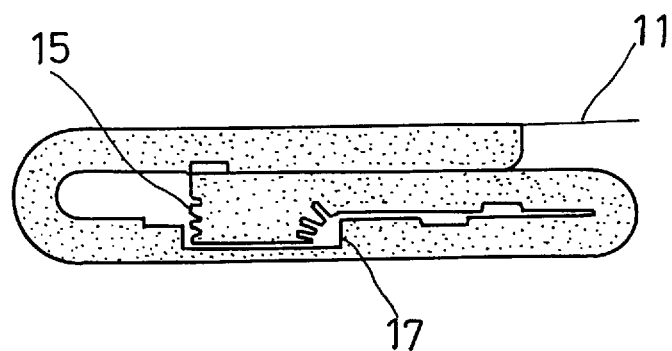
FIG. 3 shows the sanitary napkin of the invention in a folded state.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

With reference to FIGS. 1, 2A, and 2B, the sanitary napkin of the present invention comprises a body 10 having a non-permeable back layer 11 and a permeable surface layer 12 joined to the non-permeable back layer 11 along a periphery thereof. A space defined between the permeable surface layer 12 and the non-permeable back layer 11 accommodates a water absorbent body 13, which is provided with a water absorbent tissue layer 14 at an upper surface thereof. The non-permeable back layer 11 of the body 10 may also be provided with a plurality of pressure-sensitive adhesive tapes (not shown) for positioning purposes. In particular, the body 10 is projectingly provided with a stop element 15 near a rear end thereof. The stop element 15 is formed integrally with the body 10. It has a flat shape with an upper rim inclining inwardly from an outer side and, after running along a certain length, drops smoothly in a curve and lies at the same level as the body 10. Additionally, the upper surface of the body 10 may have a plurality of reinforcing grooves 16 horizontally disposed thereon.

Referring to FIG. 3, the present invention may be folded up like ordinary sanitary napkins. In order that the stop element 15 may not make the entire surface of the sanitary napkin of the invention arch, a groove 17 is provided on the body 10 at a position corresponding to that of the stop element 15 when the sanitary napkin is folded, the area of the groove 17 being slightly larger than that of the stop element 15 but the depth of the groove 17 is smaller than the height of the stop element 15. Since the interior of the stop element 15 is soft water absorbent substances, when the stop element 15 is received in the groove 17, the stop element 15 will be suitably pressed so that it may fit in the groove 17.

Figure 4:
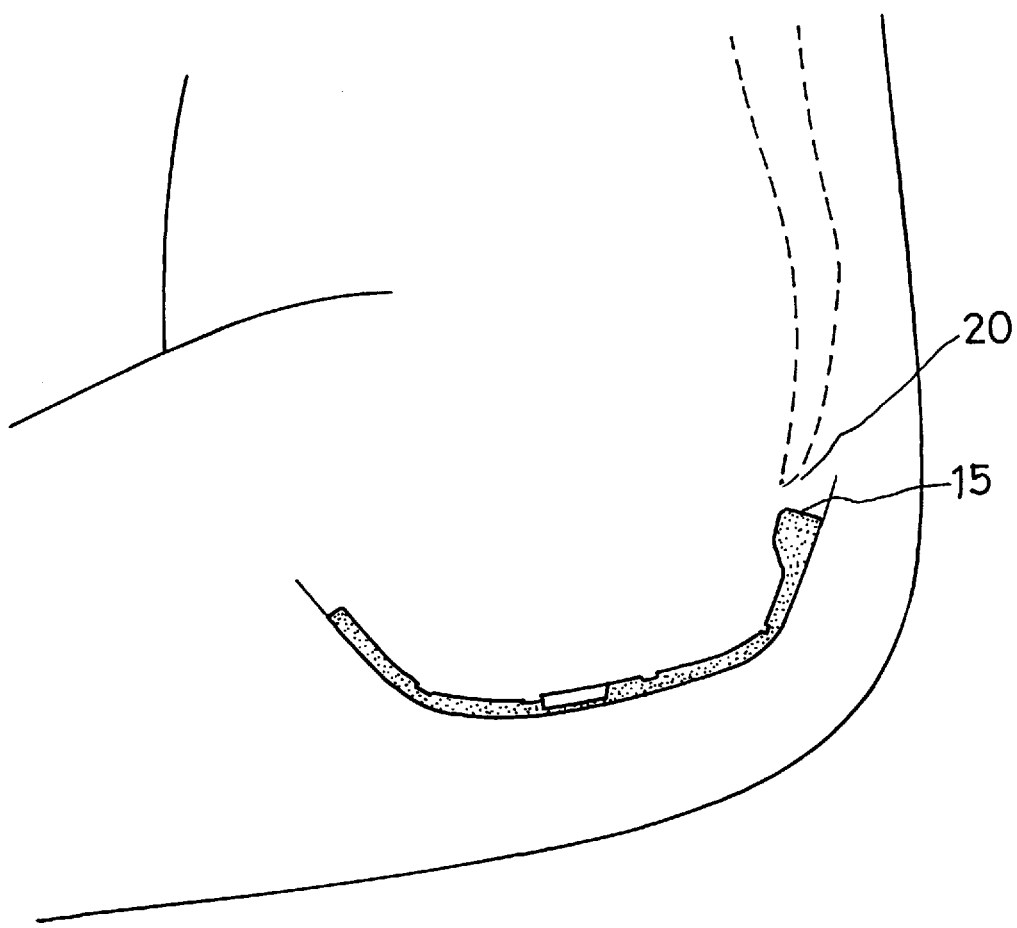
FIG. 4 illustrates use of the sanitary napkin of the present invention.

In use, referring to FIG. 4, the stop element 15 is positioned at the depressed or concave portion of the coccyx area while the rest of the sanitary napkin covers forwardly. The stop element 15 may suitably absorb menstrual discharge flowing backwardly to the coccyx area from the vaginal opening, preventing the menstrual discharge from flowing out of the sanitary napkin. At the same time, the stop element 15 may provide a suitable support and protection for the coccyx area. As for the body 10 of the sanitary napkin covering the vaginal area, since it is reinforced by reinforcing grooves 16, it will not easily deform in shape during normal use.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A sanitary napkin comprising an elongated absorbent body having an upper layer, a lower layer and a plurality of reinforcing elements thereon, said absorbent body enclosed between a non-permeable back layer on the lower layer and a permeable surface layer on the upper layer, said body further being provided with a stop element on the upper layer at one end thereof extending above the upper layer, said stop element being flat and arched in shape, which may be held at a depressed portion of the coccyx area of the user to absorb any menstrual discharge flowing to the coccyx area, said absorbent body further having a groove extending into the absorbent body for receiving said stop element when said sanitary napkin is folded.

\* \* \* \* \*